United States Patent
Brambilla

(10) Patent No.: US 8,420,060 B2
(45) Date of Patent: Apr. 16, 2013

(54) PHARMACEUTICAL AEROSOL FORMULATIONS OF FORMOTEROL AND BECLOMETASONE DIPROPIONATE

(75) Inventor: Gaetano Brambilla, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 288 days.

(21) Appl. No.: 12/897,117

(22) Filed: Oct. 4, 2010

(65) Prior Publication Data
US 2011/0081301 A1 Apr. 7, 2011

(30) Foreign Application Priority Data
Oct. 2, 2009 (EP) ................................ 09172083

(51) Int. Cl.
*A61K 9/00* (2006.01)
*A61K 9/12* (2006.01)
*A61K 9/14* (2006.01)
*A61K 31/045* (2006.01)
*A61K 31/05* (2006.01)
*A61K 31/075* (2006.01)
*A61K 31/085* (2006.01)
*A61K 31/13* (2006.01)
*A61K 31/135* (2006.01)
*A61K 31/167* (2006.01)
*A61K 31/56* (2006.01)

(52) U.S. Cl.
USPC ............... 424/46; 424/45; 424/489

(58) Field of Classification Search .......... 424/45, 424/46, 489; 514/171, 180, 659, 667, 716, 514/721, 724, 729, 731, 741
See application file for complete search history.

(56) References Cited

U.S. PATENT DOCUMENTS
6,423,298 B2 * 7/2002 McNamara et al. ............ 424/45
7,479,572 B2 * 1/2009 Tanoury et al. ................ 564/216
2005/0287076 A1 * 12/2005 Looker et al. .................. 424/46
2006/0083693 A1 4/2006 Lewis et al.

FOREIGN PATENT DOCUMENTS
EP 1 400 239 A1 3/2004
WO WO 00/53187 * 9/2000

OTHER PUBLICATIONS

Vippagunta et al. "Crystalline Solids," Advanced Drug Delivery Reviews, 2001, 48, 3-26.*
Braga et al. Chem. Commun., "Making Crystals from Crystals: a green route to crystal engineering and polymorphism," 2005, pp. 3635-3645.*
Seddon, K.R., "Pseudopolymorph: a polemic," Crystal Growth & Design, 2004, 4(6), pp. 1087, web release date Oct. 19, 2004.*
Garcia-Marcos et al. "Inhaled corticosteroids plus long-acting Beta-2-agonists as combined therapy in asthma," Expert Opinion, Apr. 1, 2003, 4(1), pp. 23-39.*
"Asthma: Lung and Airways Disorders," Merck Manual Home Edition, accessed online on May 5, 2010 at www.merck.com/"mhe/print/sec04/ch044/ch044a.html.*
"Chronic Obstructive Pulmonary Disease," Merck Manual Home Edition, accessed on Marcy 21, 2010 at www.merck.com/mmhe/print/sec04/ch045a.html.*
Office Action issued in European Patent Application No. 09172083.9 on Apr. 14, 2010.
D. Singh et al., Pulmonary Pharmacology & Therapeutics 21 (2008) pp. 551-557.
G. Huchon et al., Respiratory Medicine (2009) 103, pp. 41-49.

* cited by examiner

*Primary Examiner* — James H Alstrum Acevedo
(74) *Attorney, Agent, or Firm* — Oblon, Spivak, McClelland, Maier & Neustadt, L.L.P.

(57) ABSTRACT

Pharmaceutical formulations comprising beclometasone dipropionate and a salt of formoterol exhibit improved stability and are useful in pressurized metered dose inhalers (pMDIs).

15 Claims, 1 Drawing Sheet

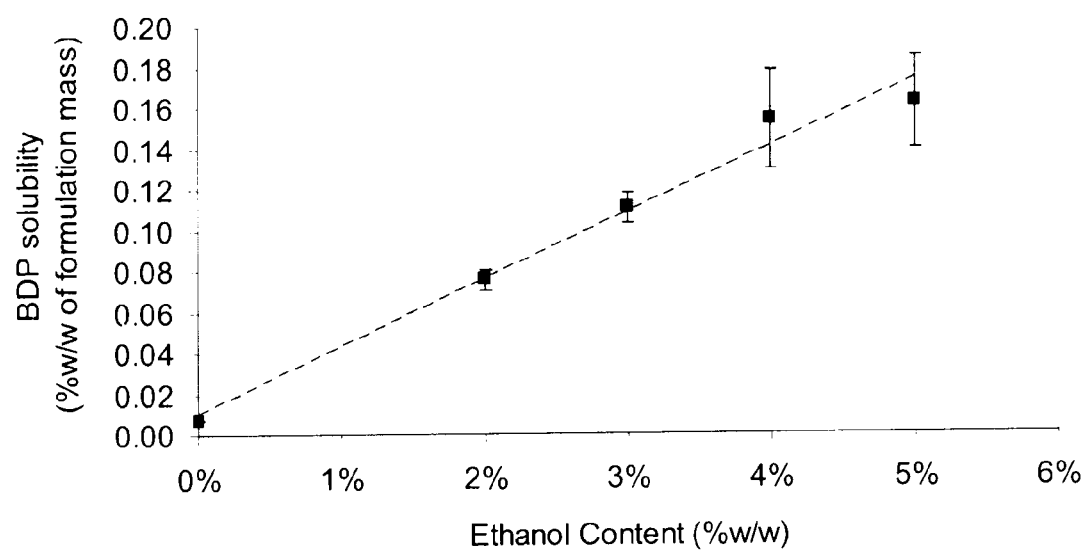

PHARMACEUTICAL AEROSOL FORMULATIONS OF FORMOTEROL AND BECLOMETASONE DIPROPIONATE

CROSS REFERENCES TO RELATED APPLICATIONS

This application claims priority to European Patent Application No. 09172083.9 filed on Oct. 2, 2009, which is incorporated herein by reference in its entirety.

BACKGROUND OF THE INVENTION

1. Field of the Invention

The present invention relates to pharmaceutical formulations for use in the administration of medicaments by inhalation. In particular, the present invention relates to pharmaceutical formulations for use in pressurized metered dose inhalers (MDIs). The present invention also relates to methods for the preparation of said pharmaceutical formulations and to the use thereof in therapy.

2. Discussion of the Background

Pressurized metered dose inhalers (pMDIs) are well known devices for administering pharmaceutical active ingredients to the respiratory tract by inhalation. They consist of containers containing multiple doses, e.g., tens or even hundreds of doses, and each of these doses is delivered by a suitable metering valve.

Formulations for pMDIs typically consist of suspensions or solutions of one or more active substances in a liquefied propellant which is utilized to expel solid particles or droplets respectively containing the active ingredient to the respiratory tract as an aerosol.

The most commonly used aerosol propellants are hydrofluoroalkanes (HFAs; known also as hydrofluorocarbons or HFCs), in particular, 1,1,1,2-tetrafluoroethane (HFA 134a) and 1,1,1,2,3,3,3-heptafluoropropane (HFA 227).

The efficiency of an aerosol device, such as a pMDI, is a function of the dose deposited at the appropriate site in the lungs. Deposition is affected by several factors, of which one of the most important is the aerodynamic particle size. Solid particles and/or droplets in an aerosol formulation can be characterized by their mass median aerodynamic diameter (MMAD).

Respirable particles are generally considered to be those with a MMAD less than 5 micron.

Active substances commonly delivered by inhalation include bronchodilators such as beta-2 adrenoreceptor agonists and anticholinergics, corticosteroids, anti-allergics and other active ingredients that may be efficiently administered by inhalation, thus increasing the therapeutic index and reducing side effects of the active material.

Formoterol, i.e., 2'-hydroxy-5'-[(RS)-1-hydroxy-2{[(RS)-p-methoxy-α-methylphenethyl]amino}ethyl]formanilide, particularly its fumarate salt, is a well known beta-2 adrenoreceptor agonist currently used clinically in the treatment of bronchial asthma and related disorders.

Beclometasone dipropionate is a potent anti-inflammatory steroid, named (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate, available under a wide number of brands for the prophylaxis and/or treatment of inflammatory respiratory disorders.

Co-administration of formoterol fumarate and beclometasone dipropionate by pressurised metered dose inhalers (pMDI's) has significant advantages in the treatment and control of asthma.

The currently marketed formulation contains both active ingredients dissolved in a mixture of HFA134a and ethanol as co-solvent.

When the formulation is in the form of solution, the volumetric contribution of suspended drug particles is absent and much finer liquid droplets clouds, largely defined by the drug concentration in the solution, are generated.

The major advantage of said solution formulation is related to the presence of the corticosteroid in solution as the fine droplets exhibit an improved lung deposition and improved penetration into the bronchioloalveolar distal part of the respiratory tree wherein inflammation is known to play a role in spontaneous exacerbations of asthma symptoms.

However, although it has the apparent pH adjusted according to the teaching of WO 01/89480 for improving its chemical stability, due to the limited stability of formoterol in solution, said formulation can be stored for no longer than 15 months at a refrigerator temperature (from +2 to +8° C.) and for no longer than 5 months at room temperature.

These stability features are not optimal, in particular in sub-tropical and tropical countries.

HFA formulations wherein formoterol is present as suspended particles would obviously encounter lesser problems of chemical stability.

On the other hand, the amount of ethanol useful for solubilizing the corticosteroid may not be appropriate or optimal for ensuring the physical stability of a suspended drug. It is indeed well known that if the suspended drug has a slight solubility in the medium, a process known as Ostwald ripening can lead to particle size growth. The effect of Ostwald ripening may be particularly severe for a drug such as formoterol which needs to be formulated in low doses.

In view of the aforementioned problems, it would be highly advantageous to provide an aerosol pharmaceutical formulation for pMDIs comprising formoterol and beclometasone dipropionate, being both chemically and physically stable to allow a longer shelf-life at room temperature than the formulation of the prior art.

SUMMARY OF THE INVENTION

Accordingly, it is one object of the present invention to provide novel aerosol pharmaceutical formulation for pMDIs which comprise a pharmaceutically acceptable salt of formoterol and beclometasone dipropionate.

It is another object of the present invention to provide novel aerosol pharmaceutical formulation for pMDIs which comprise a pharmaceutically acceptable salt of formoterol and beclometasone dipropionate being both chemically and physically stable to allow a longer shelf-life at room temperature than prior art formulations.

It is another object of the present invention to provide novel pMDIs which contain such a formulation.

It is another object of the present invention to provide novel methods for preparing such a formulation.

It is another object of the present invention to provide novel methods of treating and/or preventing certain diseases and conditions by administering such a formulation.

These and other objects, which will become apparent during the following detailed description, have been achieved by the inventor's discovery that pharmaceutical aerosol formulations for use in pMDIs which comprise:

(a) from 0.001 to 0.05% w/w of a pharmaceutically acceptable salt of formoterol or a solvate thereof;
(b) from 0.05 to 0.16% w/w of beclometasone dipropionate (BDP);
(c) from 2.0 to 4.8% w/w ethanol; and
(d) HFA 134a
characterized in that HFA 134a is the sole propellant and the salt of formoterol is suspended in a micronized form while the corticosteroid is fully dissolved, exhibit improved stability.

According to another aspect, the present invention provides a pressurized metered dose inhaler (pMDI) comprising a canister filled with the pharmaceutical formulation of the present invention, and a metering valve for delivering a therapeutically effective dose of the active ingredients.

In a further aspect, the present invention provides a method of preventing and/or treating an inflammatory or obstructive airways disease such as asthma or chronic obstructive pulmonary disease (COPD) in a mammal, which comprises administration by inhalation of an effective amount of the formulation described before.

Finally, the present invention provides the use of a corticosteroid for aerosol formulation for inhalation comprising a pharmaceutically acceptable salt of formoterol or a solvate thereof as an active ingredient and a mixture of HFA134 and ethanol as vehicle, for decreasing the solubility of said salt of formoterol in said vehicle wherein the vehicle has a polarity expressed as dielectric constant $\in_m$ comprised between about 9.5 and about 11.0, preferably between about 9.5 and about 10.5.

The corticosteroid is advantageously selected from the group of beclometasone dipropionate and solvates thereof, budesonide and epimers thereof, fluticasone and esters thereof such as propionate and furoate, mometasone furoate, flunisolide and ciclesonide, preferably beclometasone dipropionate.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the BDP solubility (% w/w) in HFA134a containing increasing amount (%, w/w) of ethanol.

DETAILED DESCRIPTION OF THE PREFERRED EMBODIMENTS

The terms "active drug", "active ingredient", "active", "active compound" "active substance", and "therapeutic agent" are used as synonymous.

Formoterol includes two asymmetric centers and hence may exist in form of four different stereoisomers; furthermore its fumarate salt may exist in two different stoichiometries, e.g. 1:1 and 2:1.

The term "formoterol fumarate" refers to the salt in which formoterol can be each of the possible isomers either in substantially pure form or admixed in any proportions, preferably as a racemic mixture of the (R,R) and (S,S) stereoisomers.

The expressions "% w/w" and "% w/v" mean the weight percentage of the component with respect to the total weight or the total volume of the composition, respectively. The "% w/w" corresponding to the "%w/v" can be calculated by determining the density of the vehicle.

"Daily therapeutically effective dose" means the quantity of active ingredient administered at one time by inhalation upon actuation of the inhaler.

"Actuation" means the release of the active ingredient from the device by a single activation (e.g. mechanical or breath).

The term "mass median aerodynamic diameter" means the diameter of 50 percent by weight of the aerosolized particles upon actuation of the inhaler.

The term "co-solvent" means a substance having a higher polarity than that of the propellant.

The expression "formulation chemically stable" means a formulation wherein the stability and the shelf-life of the active ingredient meet the requirements of the ICH Guideline Q1A referring to "Stability Testing of new Active Substances (and Medicinal Products)".

The expression "physically stable" refers to formulations in which the suspended active ingredient exhibits substantially no growth in particle size over a prolonged period, are readily redispersible and, upon redispersion, do not flocculate so quickly as to prevent its constant dosing.

The expression 'respirable fraction' refers to an index of the percentage of active particles which would reach the deep lungs in a patient.

The respirable fraction, also termed fine particle fraction, is evaluated using a suitable in vitro apparatus such as Multistage Cascade Impactor or Multi Stage Liquid Impinger (MLSI) according to procedures reported in common Pharmacopoeias. It is calculated by the ratio between the respirable dose and the delivered dose.

The delivered dose is calculated from the cumulative deposition in the apparatus, while the respirable dose (fine particle dose) is calculated from the deposition on Stages 3 (S3) to filter (AF) corresponding to particles $\leq 4.7$ microns.

According to the Global Initiative for Asthma (GINA) guidelines 2002, "mild persistent asthma" is defined as a form characterized by less than twice a week daily symptoms, less than twice a months nocturnal asthma symptoms, and a forced expiratory volume in one second ($FEV_1$) higher than 80% with a variability comprised between 20 and 30%.

The dielectric constant $\in_m$ of the solvent mixture knowing the $\in$ value of each pure solvent is estimated by the following equation:

$$\in_m = (\% \text{ solvent}_1/100)\in_1 + (\% \text{ solvent}_2/100)\in_2 + \ldots (\% \text{ solvent}_n/100)\in_n$$

The dielectric constants of pure HFA 134a and ethanol are respectively 9.51 and 25.7 (Solvay Solkane® HFA13a monograph; Duncan Q et al Dielectric Analysis of Pharmaceutical Systems, 1995, Taylor and Francis, London).

The concentrations expressed as w/w are approximate in that they do not compensate for the density mismatch between HFA13a and ethanol. However, the precise values may be readily determined by the skilled person.

The present invention provides a pharmaceutical aerosol formulation for use in pMDIs comprising:
(a) from 0.001 to 0.05% w/w of a pharmaceutically acceptable salt of formoterol or a solvate thereof;
(b) from 0.05 to 0.16% w/w of beclometasone dipropionate (BDP);
(c) from 2.0 to 4.8% w/w ethanol; and
(d) HFA 134a;
characterized in that HFA134a is the sole propellant and the salt of formoterol is suspended in a micronized form in the formulation while the corticosteroid is fully dissolved.

Preferably, the formulation comprises as active ingredients only the combination of the salt of formoterol and beclometasone dipropionate.

The salt of formoterol is preferably present as a racemic mixture of the (R,R) and (S,S) stereoisomers.

It is also preferably present in a crystalline form, more preferably with a crystallinity degree higher than 95%, even more preferably higher than 98%, as determined according to known methods.

The concentration of the salt of formoterol ranges from 0.001 to 0.05% w/w, preferably from 0.002 to 0.03% w/w, and more preferably from 0.0025 to 0.01% w/w.

The pharmaceutically acceptable salt may be advantageously selected from fumarate, maleate, xinafoate and pamoate, preferably formoterol is in the form of fumarate, more preferably formoterol fumarate dihydrate.

Advantageously, beclometasone dipropionate (BDP) may be used as anhydrous form or as solvate such as monohydrate form.

The concentration of BDP is comprised between 0.05 and 0.16% w/w, preferably between 0.06 and 0.12% w/w, and more preferably between 0.07 and 0.10% w/w.

It has been surprisingly found that, in a mixture of ethanol and HFA134a propellant sufficient for dissolving a therapeutic amount of beclometasone dipropionate, the presence of said corticosteroid significantly decreases the solubility of formoterol fumarate dihydrate hindering the occurrence of the Ostwald Ripening process, and hence the growth of the particle size.

This finding contributes to increase the physical stability of the suspended particles of the salt of formoterol over a prolonged period time.

The presence of the salt of formoterol in suspension makes the chemical stability of the formulation substantially depending on the chemical stability of dissolved BPD, and it has been found that BDP in ethanol/HFA134a mixture can be stored at room temperature without significant degradation for at least 35 months.

Moreover, the particle size of a suspended drug is controlled by the size to which the solid medicament is reduced by micronisation, while that of the dissolved drug is controlled by the size of the droplets generated upon actuation of the inhaler.

Therefore the formulation of the invention, upon actuation of the inhaler, turns out to be highly efficacious, in particular for the treatment of mild persistent asthma, yielding particles of formoterol with a MMAD in the range 2-5 μm which are known to he more potent bronchodilators, and particles of BDP with a smaller MMAD (<1.5 μm) that may easily reach the bronchioloalveolar distal part of the respiratory tree wherein inflammation is known to play a role in spontaneous exacerbations of asthma symptoms.

Contrary to the preferred teaching of the prior art suggesting the use of less polar HFA227 propellant or mixtures thereof with HFA134a for the preparation of suspended formulation, in view of the unexpected effect of BDP on the solubility of the salt of formoterol, the aerosol formulation of the invention can utilize HFA134a as the sole propellant which exhibits a higher vapor pressure. A higher pressure, in turn, may lead to more efficient atomization and finer sprays.

In summary, the advantages of the invention in some or all of its embodiments include the fact that the aerosol formulation of the invention is environmentally friendly, chemically more stable than the formulation of the prior art, less susceptible to Ostwald ripening, and hence physically stable, can deliver a high respirable fraction, due to the low content of ethanol, and can be easily and/or economically manufactured.

The vehicle of the formulation comprises a mixture of HFA134a and ethanol.

Preferably the polarity of said vehicle is comprised between about 9.5 and about 11.0, more preferably between about 9.5 and about 10.5 expressed as dielectric constant.

The amount of ethanol should be comprised between 2.0 and 4.8% w/w. Preferably said amount is comprised between 2.2 and 4.5% w/w, more preferably between 2.5% and 4.0% w/w, even more preferably between 2.6% and 3.5% w/w.

In a particular embodiment, said amount may be comprised between 3.0 and 3.5% w/w.

Advantageously, the formulation of the invention may be suitable for delivering a therapeutic amount of the salt of formoterol and beclometasone dipropionate in one or two actuations (shots) of the inhaler.

For example, the formulations will be suitable for delivering 6-12 μg formoterol (as fumarate dihydrate) per actuation, especially 6 μg or 12 μg per actuation, and 50-200 μg beclometasone dipropionate per actuation, especially 50 or 100 μg per actuation.

The formulation according to the invention will be used in association with a suitable metering valve. Advantageously, the formulation may be actuated by a metering valve capable of delivering a volume of between 50 μl and 100 μl, e.g. 50 μl, or 63 μl, or 100 μl.

The skilled person could adjust the concentration of the active ingredients within the claimed range depending on the volume of the metering valve.

For example, for a 6 μg dose formoterol (as fumarate dihydrate) and a 50 μg dose beclometasone dipropionate, when a 63 μl metering valve is used, the final concentration of formoterol fumarate dihydrate delivered per actuation would be 0.0095% (w/v), while that of BDP per actuation would be 0.079% (w/v).

For a 6 μg dose formoterol (as fumarate dihydrate) and a 100 μg dose beclometasone dipropionate, when a 100 μl metering valve is used, the final concentration of formoterol delivered per actuation would be 0.006% (w/v), while that of BDP per actuation would be 0.1% (w/v).

For a 12 μg dose formoterol (as fumarate dihydrate) and a 100 μg dose beclometasone dipropionate, when a 100 μl metering valve is used, the final concentration of formoterol delivered per actuation would be 0.012% (w/v), while that of BDP per actuation would be 0.1% (w/v).

For a 6 μg dose formoterol (as fumarate dihydrate) and a 50 μg dose beclometasone dipropionate, when a 50 μl metering valve is used, the final concentration of formoterol delivered per actuation would be 0.012% (w/v), while that of BDP per actuation would be 0.1% (w/v).

In the formulations of the present invention, the low amount of ethanol acts as a co-solvent for dissolving BDP but also assists the physical stability of the formulation.

However, the formulation of the invention may comprise low amounts of a surfactant for the purpose of further stabilizing the suspended active ingredient and valve lubrication.

Suitable known surfactants include polysorbate 20, polysorbate 80, isopropyl myristate, oleic acid, sorbitan trioleate and lecithin.

For example, amounts of lecithin or oleic acid comprised between 0.002 and 0.05% w/w may be added to the formulation.

In one embodiment, the formulation of the present invention may also comprise further active ingredients suitable for inhalation such as muscarinic receptor antagonists and PDE4 inhibitors.

The pharmaceutical formulations according to the present invention may be filled into canisters suitable for delivering pharmaceutical aerosol formulations. Canisters generally comprise a container such as plastic or plastic-coated glass bottle or preferably a metal can, for example an aluminum can which may optionally be anodized, lacquer-coated and/or plastic-coated, which container is closed with a metering valve.

Preferably, aluminum cans are utilized such those commercially available, for instance, from Presspart.

The metering valves incorporate a gasket to prevent leakage of propellant through the valve.

The gasket may comprise any suitable elastomeric material such as for example low density polyethylene, chlorobutyl, black and white butadiene-acrylonitrile rubbers, butyl rubber, neoprene, EPDM (e.g. as described in WO95/02651) and TPE (thermoplastic elastomer; e.g. described in WO 92/11190). EPDM rubbers are preferred.

Suitable valves are commercially available from known manufacturers, for example, from Valois, France, Bespak plc UK, 3M, Neotechnic Ltd UK. Preferably the Bespack valves sold under the code 000100200376 are utilized.

Conventional bulk manufacturing methods and known machinery may be employed for the preparation of large scale batches for the commercial production of filled canisters.

Each filled canister is conveniently fitted into a suitable channeling device prior to use to form a metered dose inhaler for administration of the medicament into the lungs of a patient. Suitable channeling devices comprise, for example a valve actuator and a cylindrical or cone-like passage through which medicament may be delivered from the filled canister via the metering valve to the mouth of a patient e.g. a mouthpiece actuator.

In a typical arrangement the valve stem is seated in a nozzle block which has an orifice leading to an expansion chamber. The expansion chamber has an exit orifice which extends into the mouthpiece. Actuator (exit) orifices having a diameter in the range 0.15-0.45 mm and a length from 0.30 to 1.7 mm are generally suitable.

Preferably, an orifice having a diameter from 0.2 to 0.44 mm may be used, e.g. 0.22, 0.25, 0.30, 0.33 or 0.42 mm.

In case the ingress of water into the formulation is to be avoided, it may be desired to overwrap the MDI product in a flexible package capable of resisting water ingress.

It may also be desired to incorporate a material within the packaging which is able to adsorb any propellant and co-solvent which may leak from the canister (e.g. a molecular sieve).

Optionally, the pMDI device filled with the formulation of the present invention may be utilized together with suitable auxiliary devices favoring the correct use of the inhaler.

Said auxiliary devices are commercially available and, depending on their shape and size, are known as "spacers", "reservoirs" or "expansion chambers".

Volumatic™ is, for instance, one of the most known and used reservoirs, while Aerochamber™ is one of the most used and known spacers.

A suitable expansion chamber is reported for example in WO 01/49350.

The pMDI device may also be equipped with a dose counter or a dose indicator, which counts the number of administered doses and displays either numerically or by some other means the number of remaining doses, so that the patient will be aware when the drug canister has delivered its prescribed contents.

The formulation of the present invention may also be used with common pressurized breath-activated inhalers such as those known with the registered names of Easi-Breathe™ and Autohaler™.

Administration of the aerosol formulation of the present invention may be indicated for the prevention and/or treatment of mild, moderate or severe acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis may also benefit by this kind of formulation.

In particular, as mentioned above, the aerosol formulation of the present invention may be indicated for controlling symptoms in patients affected by mild persistent asthma.

Other features of the invention will become apparent in the course of the following descriptions of exemplary embodiments which are given for illustration of the invention and are not intended to be limiting thereof.

EXAMPLES

Example 1

The solubility determination of BDP in the HFA134a/ethanol mixtures was determined according the method reported in Gupta A et al, *J. Aerosol Medicine,* 2003, 16(2), 167-174, slightly modified as follows.

Vials that contained excess BDP were prepared at 2%, 3%, 4% and 5% ethanol in HFA134a. After equilibration, the samples were filtered though a 0.2 μm PTFE filter coupled inline with Presspart standard C126 canisters fitted Bespak EPDM with a dip tube. The results are reported in the plot of FIG. 1, from which the BDP solubility can be extrapolated.

Example 2

The solubility of formoterol fumarate dihydrate in HFA134a:ethanol 97.3:2.7 (w/w) in the presence and in the absence of 0.1% w/w BDP was estimated according to the method of Example 1. The formoterol fumarate dihydrate solubility at 20° C. without BDP turned out to be about 0.005 μg/μl corresponding to about 0.0005% w/w. After addition of 50 μl of 0.1 w/w BDP solution, it decreases more than half, i.e. to 0.002 μg/μl corresponding to about 0.0002% w/w.

Comparative Example 3

The solubility of formoterol fumarate dihydrate in HFA227:ethanol 92.5:7.5 (w/w) in the presence and in the absence of BDP was estimated according to the method of Example 2. The formoterol fumarate dihydrate solubility at 20° C. without BDP turned out to be about 0.03 μg/μl corresponding to 0.003% w/w, and it does not change in the presence of BDP.

Comparative Example 4

The solubility of formoterol fumarate dihydrate in HFA227:ethanol 97.3:2.7 (w/w) in the presence and in the absence of BDP was estimated according to the method of Example 2. The formoterol fumarate dihydrate solubility at 20° C. without BDP turned out to be about 0.006 μg/μl corresponding to 0.0006% w/w, and it does not change in the presence of BDP.

Example 5

An aerosol formulation was prepared starting from micronized formoterol fumarate dihydrate obtained by milling having a MMD comprised between 2 and micron and beclometasone dipropionate as commercially available. Said formulation has the following composition:

| | |
|---|---|
| Formoterol fumarate dihydrate | 0.0095% w/w |
| Beclometasone dipropionate | 0.079% w/w |
| Ethanol | 2.7% w/w |
| HFA134 | to 100% |

This formulation was filled into an aluminum canister under pressure and fitted with a metering valve having a 63 μl metering chamber. It is suitable for delivering 6 μg formoterol and 50 μg beclometasone dipropionate per actuation.

The aerosol performances were assessed using an Andersen Cascade Impactor according to according to the procedure described in the European Pharmacopoeia $6^{th}$ edition, 2009 (6.5), part 2.09.18. Quantification of beclometasone dipropionate (BDP) and formoterol fumarate dehydrate (FF) was performed using a HPLC method. The following parameters were determined:
i) delivered dose is calculated from the cumulative deposition in the ACI, divided by the number of actuations per experiment;
ii) respirable dose (fine particle dose=FPD) is obtained from the deposition from Stages 3 (S3) to filter (AF) of the ACI, corresponding to particles of diameter ≦4.7 microns, divided by the number of actuations per experiment;
iii) respirable fraction (fine particle fraction=FPF) which is the percent ratio between the respirable dose and the delivered dose;
iv) mass median aerodynamic diameter (MMAD) which is the diameter around which the mass aerodynamic diameters of the emitted particles are distributed equally; and
v) Geometric standard deviation (GSD) which is a measure of the spread of the aerodynamic particle size distribution.

The results are summarised in Table 1.

TABLE 1

Summary of Aerosol Performances.
Data represents Mean (n = 2).

| Drug | BDP | FF |
|---|---|---|
| Delivered Dose (μg) | 46.0 | 3.9 |
| Fine particle dose (μg) | 30.0 | 2.3 |
| Fine particle fraction (%) | 64.0 | 59.3 |
| MMAD (μm) | 1.1 | 2.0 |
| GSD | 2.2 | 1.5 |

The solutions of the present invention are capable of providing, upon actuation of the pMDI device in which they are contained, a FPF much higher than 50% for both the active ingredients.

Example 6

An aerosol formulation is prepared with the following composition:

| | |
|---|---|
| Formoterol fumarate dihydrate | 0.006% w/w |
| Beclometasone dipropionate | 0.1% w/w |
| Ethanol | 3.0% w/w |
| HFA134 | to 100%1 |

This formulation is filled into an aluminum canister under pressure and fitted with a metering valve having a 100 μl metering chamber.

Example 7

An aerosol formulation may be prepared with the following composition:

| | |
|---|---|
| Formoterol fumarate dihydrate | 0.012% w/w |
| Beclometasone dipropionate | 0.1% w/w |
| Ethanol | 3.0% w/w |
| HFA134 | to 100% |

This formulation is filled into an aluminum canister under pressure and fitted with a metering valve having a 50 μl metering chamber.

Example 8

An aerosol formulation is prepared with the following composition:

| | |
|---|---|
| Formoterol fumarate dihydrate | 0.019% w/w |
| Beclometasone dipropionate | 0.16% w/w |
| Ethanol | 4.7% w/w |
| HFA134 | to 100% |

This formulation is filled into an aluminum canister under pressure and fitted with a metering valve having a 63 μl metering chamber.

Example 9

An aerosol formulation is prepared with the following composition:

| | |
|---|---|
| Formoterol fumarate dihydrate | 0.0095% w/w |
| Beclometasone dipropionate | 0.079% w/w |
| Ethanol | 2.0% w/w |
| HFA134 | to 100% |

This formulation is filled into an aluminum canister under pressure and fitted with a metering valve having a 63 μl metering chamber.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical aerosol formulation, comprising:
   (a) from 0.001 to 0.05% w/w of formoterol fumarate dihydrate;
   (b) from 0.05 to 0.16% w/v of beclometasone dipropionate;
   (c) from 2.0 to 4.8% w/w ethanol;
   (d) HFA 134a;
   wherein said HFA134a is the sole propellant and said formoterol fumarate dihydrate is suspended in a micronized form in said formulation while said beclometasone dipropionate is fully dissolved.

2. A formulation as claimed in claim 1, which comprises as active ingredients only the combination of formoterol fumarate dihydrate and beclometasone dipropionate.

3. A formulation as claimed in claim 1, which comprises from 2.5 to 4.5% w/w of ethanol.

4. A formulation as claimed in claim 3, which comprises from 2.5% to 4.0% w/w of ethanol.

5. A pressurized metered dose inhaler, comprising a canister filled with a pharmaceutical formulation according to claim 1 and a metering valve for delivering therapeutically effective doses of said formoterol fumarate dihydrate and said beclometasone dipropionate.

6. A pressurized metered dose inhaler as claimed in claim 5, wherein the dose of said formoterol fumarate dihydrate is 6 or 12 μg.

7. A pressurized metered dose inhaler as claimed in claim 5, wherein the dose of beclometasone dipropionate is 50 or 100 μg.

8. A pressurized metered dose inhaler, comprising a canister filled with a pharmaceutical formulation according to claim 2 and a metering valve for delivering therapeutically effective doses of said formoterol fumarate dihydrate and said beclometasone dipropionate.

9. A pressurized metered dose inhaler, comprising a canister filled with a pharmaceutical formulation according to claim 3 and a metering valve for delivering therapeutically effective doses of said formoterol fumarate dihydrate and said beclometasone dipropionate.

10. A pressurized metered dose inhaler, comprising a canister filled with a pharmaceutical formulation according to claim 4 and a metering valve for delivering therapeutically effective doses of said formoterol fumarate dihydrate and said beclometasone dipropionate.

11. A method for decreasing the solubility of formoterol fumarate dihydrate in an aerosol formulation for inhalation, comprising formoterol fumarate dihydrate as an active ingredient and a mixture of HFA134 and ethanol as vehicle, wherein the vehicle has a polarity expressed as dielectric constant $\in_m$ comprised between about 9.5 and about 11.0, said method comprising adding an effective amount of a corticosteroid to said formulation.

12. A method for treating an inflammatory or obstructive airway disease in a mammal, which comprises administering by inhalation an effective amount of a formulation according to claim 1, wherein said inflammatory or obstructive airway disease is asthma or chronic obstructive pulmonary disease.

13. A method for treating an inflammatory or obstructive airway disease in a mammal, which comprises administering by inhalation an effective amount of a formulation according to claim 2, wherein said inflammatory or obstructive airway disease is asthma or chronic obstructive pulmonary disease.

14. A method for treating an inflammatory or obstructive airway disease in a mammal, which comprises administering by inhalation an effective amount of a formulation according to claim 3, wherein said inflammatory or obstructive airway disease is asthma or chronic obstructive pulmonary disease.

15. A method for treating an inflammatory or obstructive airway disease in a mammal, which comprises administering by inhalation an effective amount of a formulation according to claim 4, wherein said inflammatory or obstructive airway disease is asthma or chronic obstructive pulmonary disease.

* * * * *